United States Patent

Okawa et al.

(10) Patent No.: US 6,448,360 B2
(45) Date of Patent: Sep. 10, 2002

(54) PROCESS FOR THE PRODUCTION OF CYCLIC SILOXANE

(75) Inventors: Tadashi Okawa; Junichi Maeshima; Norikatsu Higuchi; Takao Takemasa, all of Chiba Prefecture (JP)

(73) Assignee: Dow Corning Toray Silicone Co., Ltd., Tokyo (JP)

(*) Notice: Subject to any disclaimer, the term of this patent is extended or adjusted under 35 U.S.C. 154(b) by 0 days.

(21) Appl. No.: 09/765,047

(22) Filed: Jan. 19, 2001

(30) Foreign Application Priority Data

Jan. 28, 2000 (JP) ........................................ 2000-019696

(51) Int. Cl.⁷ .............................................. C08G 77/08
(52) U.S. Cl. ............................. 528/14; 556/460; 528/32
(58) Field of Search ........................... 556/460; 528/14, 528/32

(56) References Cited

U.S. PATENT DOCUMENTS

| | | | | |
|---|---|---|---|---|
| 2,860,152 A | * | 11/1958 | Fletcher | 556/460 |
| 3,846,464 A | * | 11/1974 | Razzano | 556/460 |
| 4,197,251 A | * | 4/1980 | Hirakawa et al. | 556/460 |
| 4,689,420 A | * | 8/1987 | Baile et al. | 556/460 |
| 4,764,631 A | | 8/1988 | Halm et al. | 556/460 |
| 5,109,093 A | | 4/1992 | Rees et al. | 528/14 |
| 5,188,899 A | * | 2/1993 | Matsumoto et al. | 428/405 |
| 5,420,325 A | * | 5/1995 | Razzano et al. | 556/460 |
| 5,670,689 A | | 9/1997 | Allandrieu et al. | 556/460 |
| 6,303,811 B1 | * | 10/2001 | Krahnke et al. | 556/460 |

FOREIGN PATENT DOCUMENTS

| | | | |
|---|---|---|---|
| GB | 845554 | 8/1960 | |
| JP | 42-8949 | 1/1964 | |
| JP | 48-88199 | 11/1973 | ......... C07D/109/00 |
| JP | 49-92025 | 9/1974 | ............. C07F/7/08 |
| JP | 49-124067 | 11/1974 | ............. C07F/7/21 |
| JP | 54-090120 | 7/1979 | ............. C07F/7/08 |
| JP | 54-117491 | 9/1979 | ............. C07F/7/08 |
| JP | 55-38898 | 3/1980 | ........... C08G/77/08 |
| JP | 59-222495 | 12/1984 | ............. C07F/7/21 |
| JP | 2-91126 | 9/1990 | ........... C08G/77/44 |

* cited by examiner

*Primary Examiner*—Margaret Moore
(74) *Attorney, Agent, or Firm*—Timothy J. Troy; Patricia M. Scaduto; Jim L. De Cesare

(57) ABSTRACT

A process for the production of a cyclic siloxane described by formula $$(R^1(CH_3)SiO)_d$$

comprising reacting in the presence of an alkali catalyst a siloxane mixture comprising a silane or a linear siloxane described by general formula $$HO(R^1(CH_3)SiO)_bH$$

and a cyclic siloxane described by general formula $$(R^1(CH_3)SiO)_c,$$

where $R^1$ is an alkenyl group having 6 to 14 carbon atoms, b is an integer of one or greater, c is an integer of 3 or greater, and d is an integer of 3 or greater.

6 Claims, No Drawings

PROCESS FOR THE PRODUCTION OF CYCLIC SILOXANE

BACKGROUND OF INVENTION

The present invention is a process for producing high-purity cyclic siloxane. More specifically, it is a process for producing high-purity cyclic siloxane by reducing the amount of silanol-containing linear siloxane contained as an impurity in cyclic siloxane. Cyclic siloxane can be prepared by the hydrolysis and condensation of diorganodichlorosilane or diorganocyclosilazane, and organopolysiloxane can be obtained by polymerizing such cyclic siloxane. However, linear siloxanes or silanes containing silanol groups are contained in the cyclic siloxane as impurities, and it is known that such silanes or linear siloxanes inhibit an increase in the molecular weight of the organopolysiloxane.

The authors of the present invention have attempted to use distillation in order to separate the silanol-containing linear siloxane contained in cyclic siloxane in the process of forming high molecular weight organopolysiloxane by polymerizing a cyclic siloxane having methyl groups and alkenyl groups having 6 to 14 carbon atoms. However due to the high boiling point of cyclic siloxane it has proved difficult to obtain high-purity cyclic siloxane.

It is an object of the present invention to provide a process for the production of high-purity cyclic siloxane by reducing the amount of silanol-containing linear siloxane contained as an impurity in cyclic siloxane having alkyl groups and alkenyl groups 6 to 14 carbon atoms.

SUMMARY OF INVENTION

The present invention is a process for the production of a cyclic siloxane described by formula $$(R^1(CH_3)SiO)_d$$

comprising reacting in the presence of an alkali catalyst a siloxane mixture comprising a silane or a linear siloxane described by general formula $$HO(R^1(CH_3)SiO)_bH$$

and a cyclic siloxane described by general formula $$(R^1(CH_3)SiO)_c,$$

where $R^1$ is an alkenyl group having 6 to 14 carbon atoms, b is an integer of one or greater, c is an integer of 3 or greater, and d is an integer of 3 or greater.

DESCRIPTION OF INVENTION

The present invention is a process for the production of a cyclic siloxane described by formula $$(R^1(CH_3)SiO)_d$$

comprising reacting in the presence of an alkali catalyst a siloxane mixture comprising a silane or a linear siloxane described by general formula $$HO(R^1(CH_3)SiO)_bH$$

and a cyclic siloxane described by general formula $$(R^1(CH_3)SiO)_c,$$

where $R^1$ is an alkenyl group having 6 to 14 carbon atoms, b is an integer of one or greater, c is an integer of 3 or greater, and d is an integer of 3 or greater.

The cyclic siloxane production process of the present invention is explained in detail hereinbelow. In the present process the siloxane mixture which serves as the starting material is made up of a silane or a linear siloxane described by general formula $$HO(R^1(CH_3)SiO)_bH$$

where $R^1$ is an alkenyl group having 6 to 14 carbon atoms and b is an integer of 1 or greater and a cyclic siloxane described by general formula $$(R^1(CH_3)SiO)_c$$

where $R^1$ is as described above and c is an integer of 3 or greater. In the above formulas, $R^1$ is an alkenyl group having 6 to 14 carbon atoms, exemplified by 5-hexenyl, 6-heptenyl, and 7-octenyl, with alkenyl groups having 6 to 10 carbon atoms, in particular, 5-hexenyl, being especially preferable from the standpoint of the ease of access to starting materials and the ease of synthesis. Also, b in the above formulas is an integer of 1 or greater, preferably, an integer of 1 to 50, and especially preferably, an integer of 1 to 20. Additionally, c in the above formulas is an integer of 3 or greater, preferably, an integer of 3 to 20. There are no limitations concerning the ratio of the silane or linear siloxane to the cyclic siloxane in such a siloxane mixture. This type of siloxane mixture can be represented by the average formula $$HO(R^1(CH_3)SiO)_eH$$

where $R^1$ is an alkenyl group having 6 to 14 carbon atoms, exemplified by the same groups as those mentioned above and e is a number greater than 1, preferably, a number between 1 and 30 (exclusive of 1). Such a siloxane mixture preferably has, for instance, at least 100 ppm of silanol groups, and, especially preferably, at least 1000 ppm of silanol groups.

It is preferable that such a silanol mixture be prepared by reacting a silane described by general formula $$R^1(CH_3)SiX_2$$

where $R^1$ is an alkenyl group having 6 to 14 carbon atoms and X is a hydrolyzable group or a cyclic silazane described by general formula $$(R^1(CH_3)SiNR^2)_a$$

where $R^1$ is the same as described above, $R^2$ is a hydrogen atom or a monovalent hydrocarbon group, and a is an integer of 3 or greater with an equivalent or greater quantity of water. The reaction consists in a hydrolysis of the above-mentioned silane or cyclic silazane and a subsequently occurring condensation reaction.

In the silane described by general formula $$R^1(CH_3)SiX_2,$$

$R^1$ is an alkenyl group having 6 to 14 carbon atoms exemplified by the same groups as those mentioned above. Also, X in the formula above is a hydrolyzable group, exemplified by chlorine, bromine, iodine, and other halogen atoms; acetoxy, acryloxy, methacryloxy, and other acyloxy groups; methoxy, ethoxy, propoxy, and other alkoxy groups; amino groups; methylamino, ethylamino, dimethylamino, diethylamino, and other substituted amino groups. Such silane is exemplified by hexenylmethyldichlorosilane, heptenylmethyldichlorosilane, octenylmethyldichlorosilane, hexenylmethyldibromosilane, hexenylmethyldiiodosilane, hexenylmethyldiacetoxysilane, hexenylmethyldimethoxysilane, hexenylmethyldimethoxysilane, and hexenylmethylbis(dimethylamino)silane.

In the cyclic silazane described by general formula $$(R^1(CH_3)SiNR^2)_a,$$

$R^1$ is an alkenyl group having 6 to 14 carbon atoms exemplified by the same groups as those mentioned above. Also, $R^2$ in the above formula is a hydrogen atom or a monovalent hydrocarbon group, with the monovalent hydrocarbon group of $R^2$ exemplified by methyl, ethyl, propyl, and other alkyl groups; vinyl, allyl, butenyl, and other alkenyl groups; phenyl, tolyl, and other aryl groups; and benzyl, phenethyl, and other aralkyl groups. Also, a in the formula above is an integer of 3 or greater, preferably an integer of 3 to 10. Such cyclic silazane is exemplified by the following compounds.

$$(CH_2=CHCH_2CH_2CH_2CH_2(CH_3)SiNH)_3,$$

$$(CH_2=CHCH_2CH_2CH_2CH_2(CH_3)SiNH)_4,$$

$$(CH_2=CHCH_2CH_2CH_2CH_2(CH_3)SiN(CH_3))_4.$$

The present process is characterized by causing the above-mentioned siloxane mixture to react using an alkali catalyst. The reaction consists in the cleavage of siloxane bonds followed by a rearrangement reaction (rearrangement) leading to recombination, or a condensation reaction among silanol groups. In the present process the alkali catalyst is exemplified by potassium hydroxide, sodium hydroxide, lithium hydroxide, cerium hydroxide, and other alkali metal hydroxides; sodium trimethylsilanolate, potassium trimethylsilanolate, potassium dimethylpolysiloxanolate, and other alkali metal silanolates. There are no limitations concerning the amount of addition of the alkali catalyst, however, an amount such that the quantity of the alkali metal in the catalyst is 0.00~0.05 parts by weight is preferable from the standpoint of the higher rate of reaction as well as the ease of neutralizing the alkali catalyst after the reaction.

In the present process the above-mentioned reaction can be carried out in the absence of a solvent, but it is preferable to conduct it in the presence of an aprotic organic solvent in order to selectively produce cyclic siloxane from a siloxane mixture consisting of a silane or a linear siloxane and a cyclic siloxane. Furthermore, it is preferable to conduct the above-mentioned reaction at the reflux temperature of the aprotic organic solvent in order to subject the by-produced water to azeotropic distillation. Hexane, heptane, octane, and other aliphatic hydrocarbons, as well as benzene, toluene, xylene, and other aromatic hydrocarbons are suggested as examples of such aprotic organic solvents. Although there are no limitations concerning the amount of addition of the aprotic organic solvent, it is preferable to add an amount sufficient to at least efficiently remove the by-produced water from the reaction system. In addition, because the purity of the cyclic siloxane can be further enhanced by using a larger quantity of aprotic organic solvent, it is preferable to use the aprotic organic solvent in a quantity equivalent or greater than that of the siloxane mixture.

In addition, it is preferable to use a polar aprotic organic solvent, because this can promote the above-mentioned reaction. Tetrahydrofuran, 1,4-dioxane, ethylene glycol dimethyl ether, diethylene glycol dimethyl ether, dimethylformamide, dimethylsulfoxide, and hexamethylphosphortriamide are suggested as examples of such polar aprotic organic solvents. It is preferable to use a necessary minimum amount of solvent, because if a large amount of the polar aprotic organic solvent is used the by-produced water ends up dissolved therein which makes the removal of the water from the reaction system difficult. The amount of the polar aprotic organic solvent is preferably such that it constitutes not more than 10 wt %, and especially preferably not more than 5 wt % relative to the siloxane mixture.

In the present process when an aprotic organic solvent is used the reaction temperature can be made considerably lower. Although there are no limitations concerning the temperature of the reaction in the present process, generally it is preferable for the temperature to be in the range of from 100° C. to 160° C.

In the present process, the progress of the reaction can be monitored using gas chromatography (GLC) and gel permeation chromatography (GPC). In addition, the reaction end point can be determined as the point in time at which all changes as measured by GLC and GPC end. The above-mentioned reaction can be terminated by neutralizing the alkali catalyst by adding acid. Phosphoric acid, moist carbon dioxide, and other inorganic acids; acetic acid, propionic acid, and other organic acids; trimethylchlorosilane, dimethyldichlorosilane, and other chlorosilanes are suggested as examples of the acids used as neutralizing agents. The target cyclic siloxane described by general formula $(R^1(CH_3)SiO)_c$ can be obtained by separating the byproduct salts by filtration, washing, or other means, removing the solvent and other low-boiling substances by heating under reduced pressure, and if necessary refining the product by means of distillation or other methods. $R^1$ in the formula above is an alkenyl group having 6 to 14 carbon atoms exemplified by the same groups as those mentioned above. Also, c in the above formula is an integer of 3 or greater, preferably an integer of 3 to 20. The present process permits preparation of cyclic siloxane with a silanol group content of 50 ppm or less and high molecular weight organopolysiloxanes can be obtained from such cyclic siloxane.

The present process for the production of cyclic siloxane is explained in further detail by referring to the below provided application examples. In the examples all percentages (%) are based upon weight.

Reference Example 1. 40 g Of toluene and 371 g of water were placed in a 1-L flask equipped with a stirrer, a thermometer, and a cooling tube. After that, 252 g of 5-hexenylmethyldichlorosilane were added thereto in a dropwise manner while stirring the toluene and water. Upon termination of the dropwise addition the mixture was allowed to stand to cause it to undergo phase separation and the water layer was removed and the organic layer was washed three times. 1.3 g Of sodium hydrogencarbonate was added to the organic layer after thoroughly stirring the mixture it was filtered. Toluene was removed by heating the filtrate under reduced pressure thereby obtaining 164 g of a colorless transparent liquid. When the liquid was subjected to $^{29}$Si—Nuclear Magnetic Resonance ($^{29}$Si—NMR) analysis it was found to be a siloxane mixture described by average formula $$HO(CH_2=CHCH_2CH_2CH_2CH_2(CH_3)SiO)_{13.1}H$$

having a silanol group content of 1.8 wt % and consisting of 5-hexenylmethylcyclosiloxane and a 5-hexenylmethylsiloxane oligomer having both terminal ends of the molecular chain blocked by silanol groups.

Application Example 1. 675 g Of xylene, 756 g of the siloxane mixture prepared in Reference Example 1, and 0.14 g potassium hydroxide in powder form were placed in a 2-L flask equipped with a stirrer, a thermometer, and a cooling tube. The mixture was refluxed under heating to cause it to react while removing the by-produced water by means of azeotropic distillation. As soon as water elution stopped, 28 g of dimethylformamide were added to the mixture and refluxing under heating was continued in order to elute water and then the mixture was cooled down. After neutralizing the potassium hydroxide using a sufficient quantity of carbon dioxide gas, the mixture was subjected to filtration and xylene was removed from the filtrate by heating it under reduced pressure thereby obtaining 695 g of a pale yellow transparent liquid. When the liquid was subjected to $^{29}$Si—NMR analysis, it was found to be a mixture consisting of 2.8% 5-hexenylmethylcyclosiloxane described by formula $$(CH_2=CHCH_2CH_2CH_2CH_2(CH_3)SiO)_3,$$

72.9% 5-hexenylmethylcyclosiloxane described by formula $$(CH_2=CHCH_2CH_2CH_2CH_2(CH_3)SiO)_4,$$

18.4% 5-hexenylmethylcyclosiloxane described by formula $$(CH_2=CHCH_2CH_2CH_2CH_2(CH_3)SiO)_5,$$

and 5.9% 5-hexenylmethylcyclosiloxane described by formula $$(CH_2=CHCH_2CH_2CH_2CH_2(CH_3)SiO)_6,$$

and when the mixture was analyzed using an infrared spectrophotometer (IR), it was found that the content of silanol groups in the mixture was 47 ppm.

Practical Example 1. 1.58 kg Of the 5-hexenylmethylcyclosiloxane mixture prepared in Application Example 1, 38.28 kg of octamethylcyclotetrasiloxane, 80 g of a dimethylpolysiloxane having both terminal ends of the molecular chain blocked by trimethylsiloxy groups, described by average formula $$(CH_3)_3SiO((CH_3)_2SiO)_8Si(CH_3)_3,$$

and 72 g potassium polysiloxanolate described by average formula $$KO((CH_3)_2SiO)_{37}K$$

were placed in a 50-L vessel equipped with a high-torque stirrer, a thermometer, and a cooling pipe. The mixture was heated to 150° C. under atmospheric pressure and the reaction was conducted for 6 hours. After that, a neutralization reaction was carried out by bubbling carbon dioxide gas from the bottom of the reaction vessel for 1 hour at a rate of 500 L/hr. Subsequently, to remove octamethylcyclotetrasiloxane and other low-boiling components, treatment was conducted for 2 hours under a reduced pressure at 10 Torr and 150° C. After cooling, 36 kg of a gummy colorless transparent liquid was obtained. When the liquid was analyzed using a Fourier transform infrared spectrophotometer (FTIR), it was found that it was a copolymer of 5-hexenylmethylsiloxane and a dimethylsiloxane having both terminal ends of the molecular chain blocked by trimethylsiloxy groups with a content of silanol groups of 50 ppm and a content of 5-hexenyl groups of 2.32%. In addition, when the copolymer was analyzed using gel permeation chromatography (GPC, it was found to have a weight average molecular weight of 279,000 and a number average molecular weight of 164,000.

Practical Example 2. 1.58 kg Of the 5-hexenylmethylcyclosiloxane mixture prepared in Application Example 1, 38.28 kg of octamethylcyclotetrasiloxane, 80 g of a dimethylpolysiloxane having both terminal ends of the molecular chain blocked by trimethylsiloxy groups described by average formula $$(CH_3)_3SiO((CH_3)_2SiO)_8Si(CH_3)_3,$$

and 400 g of tetramethylammonium siloxanolate described by average formula $$(CH_3)_4NO((CH_3)_2SiO)_{100}N(CH_3)_4$$

were placed in a 50-L vessel equipped with a high-torque stirrer, a thermometer, and a cooling pipe. The mixture was heated to 90° C. under atmospheric pressure and the reaction was conducted for 3 hours. Subsequently, after increasing the temperature to 150° C, treatment was conducted for 2 hours under a reduced pressure of 10 Torr and 150° C. to remove octamethylcyclotetrasiloxane and other low-boiling components. After cooling, 36.2 kg of a gummy colorless transparent liquid was obtained. When the liquid was analyzed using a FTIR spectrophotometer it was found that it was a copolymer of 5-hexenylmethylsiloxane and a dimethylsiloxane having both terminal ends of the molecular chain blocked by trimethylsiloxy groups, with a content of silanol groups of 53 ppm and a content of 5-hexenyl groups of 2.32%. In addition when the copolymer was analyzed using GPC, it was found to have a weight average molecular weight of 298,000 and a number average molecular weight of 175,000.

Practical Example 3. The 5-hexenylmethylcyclosiloxane mixture prepared in Application Example 1 at a rate of 0.206 kg/hr, octamethylcyclotetrasiloxane at a rate of 5 kg/hr, dimethylpolysiloxane having both terminal ends of the molecular chain blocked by trimethylsiloxy groups described by average formula $$(CH_3)_3SiO((CH_3)_2SiO)_8Si(CH_3)_3$$

at a rate of 10.4 g/hr, and potassium polysiloxanolate described by average formula $$KO((CH_3)_2SiO)_{37}K$$

at a rate of 9.4 g/hr, were continuously supplied to a 10-L hermetically sealed vessel heated to 165° C. A neutralization reaction was carried out using a sufficient quantity of carbon dioxide gas at the outlet of the reaction vessel. Subsequently, the solution was fed to a reduced-pressure pot at 10 Torr and 165° C. to remove octamethylcyclotetrasiloxane and other low-boiling components. After cooling, a gummy colorless transparent liquid was obtained. When the liquid was analyzed using a FTIR spectrophotometer it was found that it was a copolymer of 5-hexenylmethylsiloxane and dimethylsiloxane having both terminal ends of the molecular chain blocked by trimethylsiloxy groups, with a content of silanol groups of 48 ppm and a content of 5-hexenyl groups of 2.32%. When the copolymer was analyzed using GPC it was found to have a weight average molecular weight of 285,000 and a number average molecular weight of 168,000.

Comparative Practical Example 1. 1.58 kg Of the siloxane mixture prepared in Reference Example 1, 38.28 kg of octamethylcyclotetrasiloxane, 80 g of a dimethylpolysiloxane having both terminal ends of the molecular chain blocked by trimethylsiloxy groups described by average formula $$(CH_3)_3SiO((CH_3)_2SiO)_8Si(CH_3)_3,$$

and 72 g of potassium polysiloxanolate described by average formula

KO((CH$_3$)$_2$SiO)$_{37}$K were placed in a 50-L vessel equipped with a high-torque stirrer, a thermometer, and a cooling pipe. The mixture was heated to 150° C. under atmospheric pressure and the reaction was conducted for 6 hours. After that, a neutralization reaction was carried out by bubbling carbon dioxide gas from the bottom of the reaction vessel for 1 hour at a rate of 500 L/hr. Subsequently, to remove octamethylcyclotetrasiloxane and other low-boiling components, treatment was conducted for 2 hours under reduced pressure state at 10 Torr and 150° C. After cooling, 36 kg of a colorless transparent liquid was obtained. When the liquid was analyzed using a FTIR spectrophotometer it was found that it was a copolymer of 5-hexenylmethylsiloxane and dimethylsiloxane having both terminal ends of the molecular chain blocked by trimethylsiloxy groups, with a content of silanol groups of 167 ppm and a content of 5-hexenyl groups of 2.31%. In addition when the copolymer was analyzed using GPC it was found to have a weight average molecular weight of 204,000 and a number average molecular weight of 118,000.

Comparative Practical Example 2. 1.58 kg Of the siloxane mixture prepared in Reference Example 1, 38.28 kg of octamethylcyclotetrasiloxane, 80 g of a dimethylpolysiloxane having both terminal ends of the molecular chain blocked by trimethylsiloxy groups described by average formula (CH$_3$)$_3$SiO((CH$_3$)$_2$SiO)$_8$Si(CH$_3$)$_3$, and 400 g of tetramethylammonium siloxanolate described by average formula (CH$_3$)$_4$NO((CH$_3$)$_2$SiO)$_{100}$N(CH$_3$)$_4$ were placed in a 50-L vessel equipped with a high-torque stirrer, a thermometer, and a cooling pipe. The mixture was heated to 90° C. under atmospheric pressure and the reaction was conducted for 3 hours. However, although the start of the polymerization reaction was detected it stopped halfway and it was impossible to obtain a copolymer with a high degree of polymerization consisting of 5-hexenylmethylsiloxane and a dimethylsiloxane having both terminal ends of the molecular chain blocked by trimethylsiloxy groups.

We claim:

1. A process for the production of a cyclic siloxane described by formula (R$^1$(CH$_3$)SiO)$_d$ comprising reacting in the presence of an alkali catalyst and a polar aprotic organic solvent, a siloxane mixture comprising a silane or a linear siloxane described by general formula HO(R$^1$(CH$_3$)SiO)$_b$H and a cyclic siloxane described by general formula (R$^1$(CH$_3$)SiO)$_c$, where R$^1$ is an alkenyl group having 6–14 carbon atoms, b is an integer of one or greater, c is an integer of 3 or greater, and d is an integer of 3 or greater.

2. The process of claim 1 where R$^1$ is an alkenyl group having 6–10 carbon atoms.

3. The process of claim 1 where R$^1$ is a 5-hexenyl group.

4. The process of claim 1 where the siloxane mixture is obtained by reacting a silane described by general formula R$^1$(CH$_3$)SiX$_2$ or a cyclic silazane described by general formula (R$^1$(CH$_3$)SiNR$^2$)$_a$, where R$^1$ is an alkenyl group having 6–14 carbon atoms, X is a hydrolyzable group, R$^2$ is a hydrogen atom or a monovalent hydrocarbon group, and a is an integer of 3 or greater, with an equivalent or greater quantity of water.

5. The process of claim 1 where b is an integer of 1–50.

6. The process of claim 1 where the alkali catalyst is an alkali metal hydroxide or an alkali metal silanolate.

* * * * *